United States Patent
Abe et al.

(10) Patent No.: US 8,221,823 B2
(45) Date of Patent: Jul. 17, 2012

(54) METHOD FOR FABRICATING MATERIAL

(75) Inventors: Yoshinori Abe, Hiroshima (JP);
Tatsuyuki Nakatani, Hiroshima (JP);
Keishi Okamoto, Hiroshima (JP); Kohei Shiraishi, Hiroshima (JP); Kazuo Sugiyama, Hiroshima (JP)

(73) Assignee: Toyo Advanced Technologies Co., Ltd., Hiroshima-shi (JP)

( * ) Notice: Subject to any disclaimer, the term of this patent is extended or adjusted under 35 U.S.C. 154(b) by 249 days.

(21) Appl. No.: 12/697,581

(22) Filed: Feb. 1, 2010

(65) Prior Publication Data
US 2010/0136212 A1 Jun. 3, 2010

Related U.S. Application Data

(62) Division of application No. 10/594,918, filed as application No. PCT/JP2005/005534 on Mar. 25, 2005, now abandoned.

(30) Foreign Application Priority Data

Mar. 30, 2004 (JP) ................................. 2004-100186

(51) Int. Cl.
*A61L 33/00* (2006.01)
(52) U.S. Cl. ...................... 427/2.24; 427/2.25; 427/2.28; 427/2.31; 427/488; 427/577
(58) Field of Classification Search .................. 427/2.24, 427/2.25, 2.28, 2.31, 488, 577
See application file for complete search history.

(56) References Cited

U.S. PATENT DOCUMENTS

| | | | |
|---|---|---|---|
| 5,026,607 A | 6/1991 | Kiezulas | |
| 5,296,566 A * | 3/1994 | Brown-Wensley et al. | .. 526/171 |
| 5,489,303 A | 2/1996 | Sasaki et al. | |
| 5,491,028 A * | 2/1996 | Sarin et al. | ..................... 428/408 |
| 5,763,072 A | 6/1998 | Kato et al. | |
| 5,932,299 A * | 8/1999 | Katoot | ........................... 427/508 |
| 5,981,297 A | 11/1999 | Baselt | |
| 6,083,570 A | 7/2000 | Lemelson et al. | |
| 6,110,329 A * | 8/2000 | Holleck et al. | ............. 204/192.15 |
| 6,120,972 A * | 9/2000 | Iwanaga et al. | ............. 430/270.1 |
| 6,197,120 B1 | 3/2001 | David | |
| 6,287,285 B1 | 9/2001 | Michal et al. | |
| 6,368,658 B1 | 4/2002 | Schwarz et al. | |
| 6,379,383 B1 * | 4/2002 | Palmaz et al. | ................. 623/1.49 |
| 6,468,642 B1 | 10/2002 | Bray et al. | |
| 6,537,310 B1 * | 3/2003 | Palmaz et al. | ................. 623/1.13 |
| 6,607,908 B1 | 8/2003 | Tanga et al. | |
| 6,638,259 B1 * | 10/2003 | Palasis et al. | ................... 604/264 |
| 6,660,533 B2 * | 12/2003 | Mallet et al. | ................... 436/518 |
| 6,761,736 B1 * | 7/2004 | Woo et al. | ..................... 623/2.42 |
| 2001/0044030 A1 | 11/2001 | Veerasamy et al. | |
| 2003/0044546 A1 * | 3/2003 | Lahann et al. | ................. 427/509 |
| 2003/0104028 A1 | 6/2003 | Hossainy et al. | |
| 2003/0134132 A1 * | 7/2003 | Winterton et al. | ............ 428/451 |
| 2007/0198081 A1 * | 8/2007 | Castro et al. | ................. 623/1.42 |

FOREIGN PATENT DOCUMENTS

| | | |
|---|---|---|
| JP | 9-52707 A | 2/1997 |
| JP | 10-248923 A | 9/1998 |
| JP | 2001-139532 A | 5/2001 |
| WO | WO 00/10622 A1 | 3/2000 |
| WO | WO 02/080996 A1 | 10/2002 |

OTHER PUBLICATIONS

Steffen, Hans Joachim, et al., "Biocompatible surfaces by immobilization of heparin on diamond-like carbon films deposited on various substrates". Surface and Interface Analysis, 29, 386-391 (2000).*
Grill, A., "Diamond-like carbon coatings as biocompatible materials—an overview." Diamond and Related Materials 12 (2003) 166-170.*
Narayan, Roger J., "Nanostructured diamondlike carbon thin films for medical applications". Materials Science and Engineering C 25 (2005) 405-416.*
Gutensohn, K., et al., "In Vitro Analyses of Diamond-like Carbon Coated Stents: Reduction of Metal Ion Release, Platelet Activation, and Thrombogenicity". Thrombosis Research 99 (2000) 577-585.*
Ito et al., vol. 3, No. 1, (1985), Biomaterial, pp. 45-53.
H.J. Steffen et al., Surface and Interface Analysis, vol. 29, pp. 386-391 (2000).
Lasseter et al., "Covalently Modified Silicon and Diamond Surfaces: Resistance to Nonspecific Protein Adsorption and Optimization for Biosensing," J. Am. Chem. Soc. 2004, 126, 10220-10221.
Hamers et al., "Photochemical Functionalization of Diamond Films," Langmuir 2002, 18, 968-971.
Suto et al., "Crystal Structures of Novel Vascular Endothelial Growth Factors (VEGF) from Snake Venom," Published Nov. 12, 2004, The Journal of Biological Chemistry, vol. 280, No. 3, 2126-2131, 2005.
European Search Report issued Oct. 12, 2011, in European Patent Application No. 05727139.7.

* cited by examiner

*Primary Examiner* — Bret Chen
(74) *Attorney, Agent, or Firm* — Birch, Stewart, Kolasch & Birch, LLP

(57) ABSTRACT

A diamond-like carbon film (DLC film) is formed on the surface of a base material made of an inorganic material, such as ceramics, or the like, or an organic material, such as resin, or the like. The surface of the resultant DLC film is treated with plasma, or the like, so as to be activated. Various monomers having biocompatibility, etc., are graft-polymerized to the activated surface of the DLC film, whereby a polymer layer is formed from the monomers grafted to the surface of the DLC film. Thus, the base material coated with the DLC film modified with a polymer which does not readily separate can be realized.

15 Claims, 2 Drawing Sheets

METHOD FOR FABRICATING MATERIAL

CROSS-REFERENCE TO RELATED APPLICATIONS

The present application is a 37 CFR §1.53(b) divisional of U.S. application Ser. No. 10/594,918 filed Sep. 29, 2006 now abandoned, which is the National Phase of PCT International Application No. PCT/JP2005/005534 filed Mar. 25, 2005, which claims priority on Japanese Application No. 2004-100186 filed Mar. 30, 2004. The entire contents of each of these applications are hereby incorporated by reference.

TECHNICAL FIELD

The present invention relates to a method for treating the surface of a material with a diamond-like carbon film formed thereon, a surface-treated material, a medical material having excellent biocompatibility, and a medical instrument.

BACKGROUND ART

The diamond-like carbon film (DLC film) has a hard, fine and inert surface. Therefore, when formed on the surface of a material, for example, an inorganic material, such as a metal, ceramic, etc., or an organic material, such as a resin, etc., the DLC film can give the surface of the material certain characteristics, such as abrasion resistance, corrosion resistance, surface smoothness, etc.

For example, it has been known that coating the surface of a mold or tool with a DLC film improves the durability and releasability. Further, the coating creates a very smooth and inert surface and therefore has been a promising surface treatment for materials of medical instruments which should not cause interactions with biosubstances (see, for example, Patent Document 1 and Non-Patent Document 1).

Meanwhile, modifying the surface of a material with various substances to achieve high functionality on the material surface has been studied. With this, for example, development of nanodevices for molecular recognition on a semiconductor surface modified with functionality components, development of antithrombotic medical materials where the surface of the materials is modified with an antithrombotic material.

Various studies have been conducted especially on the means for providing biocompatibility, such as antithrombogenicity, etc., to the surface of a medical material. For example, it has been known that a hydrogel layer similar to the surface of a biomembrane can be formed on the surface of a medical material by modifying the surface of the medical material with a polymer containing as one component an artificial material having a chemical structure similar to the components of the biomembrane, such as 2-methacryloyloxyethyl phosphorylcholine (MPC), o-methacryloyl-L-Serine (SerMA), or the like, whereby excellent biocompatibility can be given to the surface of the medical material.

The surface of the material which is to be modified by such a functionality component is preferably refractory and inert. When the material surface has high reactivity, there is a possibility that an interaction between the material surface and a functionality molecule as a modifier denatures and deactivates the modifier functionality component. Further, certain environments degrade the material itself. Therefore, a material coated with a very smooth, inert DLC film is expected to exhibit excellent quality as a material which is to be modified with a functionality component, etc.

[Patent Document 1] Japanese Laid-Open Patent Publication No. 10-248923

[Non-Patent Document 1] Haruo Ito et al., "Biomaterial", 1985, Vol. 3, pp. 45-53

DISCLOSURE OF INVENTION

Problems to be Solved by the Invention

However, the DLC film is smooth and inert and is therefore difficult to modify with a functionality component, such as a biocompatible material, or the like. Since the surface is very inert, it is almost impossible to cause a chemical reaction between the surface and a functionality component for generating a covalent bond therebetween. The very smooth surface is almost incapable of physical adsorption. Even if a functionality component is temporarily adsorbed by the surface, the component immediately separates from the surface.

The present invention provides a solution to the above-described problem. An objective of the present invention is to realize a material where a base material is coated with a DLC film stably modified for a long term with a functionality component, typically a biocompatible material, and a medical material having persistent, excellent biocompatibility.

Means for Solving the Problems

To achieve the above objective, according to the present invention, the base material is coated with a diamond-like carbon film (DLC film) to which a functionality component, typically a biocompatible material, is grafted.

Specifically, a material of the present invention includes: a diamond-like carbon film formed on a surface of a base material; and a polymer grafted to a surface of the diamond-like carbon film. Since the material of the present invention includes the polymer grafted to the surface of the DLC film, the polymer does not separate from the DLC film. Therefore, it is possible to modify the surface of the base material with the polymer stably for a long term.

The first medical material of the present invention includes a biocompatible component chemically bonded to a surface of a diamond-like carbon film formed on a surface of a base material.

According to the first medical material, the biocompatible component is bonded to the surface of the DLC film formed on the surface of the base material. Therefore, excellent biocompatibility can be given to the surface of the DLC film. The biocompatible component is chemically bonded to the surface of the DLC film and does not readily separate from the surface of the DLC film. Since the DLC film is capable of a hard, dense coating over the surface of various base materials, the DLC film itself does not separate, so that deterioration of the base material itself can be suppressed. As a result, it is possible to realize a medical material which exhibits stable biocompatibility for a long term such that the biocompatible component does not separate.

In the first medical material, the biocompatible component is preferably a polymer introduced by graft polymerization to the surface of the diamond-like carbon film.

With such a structure, it is possible to introduce a variety of freely designed molecules to the surface of the DLC film.

In the first medical material, the biocompatible component may be a polymer formed by grafting vinylmonomers which contain fluorine to the surface of the diamond-like carbon film, or may be a molecule containing silicon. The biocompatible component may be bonded by a covalent bond to the surface of the diamond-like carbon film or may be bonded by an ionic bond to the surface of the diamond-like carbon film. With such structures, it is possible to surely obtain a medical material in which separation of the biocompatible component from the DLC film does not occur.

In the first medical material, the biocompatible component preferably contains at least one functional group selected from a group consisting of an ethylene oxide group, a hydroxy group, a phosphate group, an amino group, an amido group, a phosphorylcholine group, a sulfone group, and a carboxyl group. With such functional groups contained, the biocompatibility can be surely given to the surface of the medical material.

In the first medical material, an intermediate layer may be provided between the base material and the diamond-like carbon film to improve adhesion between the base material and the diamond-like carbon film. With such a structure, the surface of the base material can be more firmly coated with the DLC film. The intermediate layer is preferably an amorphous film containing silicon and carbon as primary constituents.

The second medical material of the present invention includes a hydrophilic functional group introduced to a surface of a diamond-like carbon film formed on a surface of a base material. According to the second medical material, the hydrophilic functional group is introduced to the surface of the DLC film, so that the DLC film itself exhibits hydrophilicity. Therefore, it is possible to achieve a medical material which exhibits stable biocompatibility for a long term.

In the medical material of the present invention, the base material is preferably a metal material, ceramic material, or macromolecular material, or a complex thereof.

A medical instrument of the present invention is formed by using the medical material of the present invention. With such a structure, a medical instrument having excellent biocompatibility can be obtained.

The medical instrument of the present invention is preferably a medical instrument which is to be embedded in a living body. The medical instrument may be a catheter, guide wire, stent, artificial cardiovalvular membrane, or artificial joint.

The first material surface treating method of the present invention, includes: a diamond-like carbon film formation step of forming a diamond-like carbon film on a surface of a base material; an activation step of generating on a surface of the diamond-like carbon film a reactive region which serves as a polymerization starting point; and a polymerization step of polymerizing monomers using the polymerization starting point to graft the monomers to the surface of the diamond-like carbon film.

The first material surface treating method of the present invention includes the activation step of generating on a surface of the diamond-like carbon film a reactive region which serves as a polymerization starting point and the step of polymerizing monomers using the polymerization starting point. Therefore, it is possible to graft the polymer to the surface of the inert diamond-like carbon film. It is possible to modify the surface of the DLC film with the polymer stably for a long term. It is possible to give both the characteristics of the DLC film, such as durability, etc., and the characteristics of the polymer.

The first material surface treating method preferably includes, before the diamond-like carbon film formation step, an intermediate layer formation step of forming on the surface of the base material an intermediate layer for improving adhesion between the base material and the diamond-like carbon film. With this, it is possible to surely coat the surface of the base material with the DLC film. In the intermediate layer formation step, the intermediate layer is preferably formed of an amorphous film containing silicon and carbon as primary constituents.

In the first material surface treating method, the activation step is preferably the step of generating a free radical as the polymerization starting point. The activation step is preferably a plasma irradiation step of irradiating the surface of the diamond-like carbon film with plasma. With these features, the polymerization starting point can be surely generated on the surface of the DLC film. The plasma irradiation step preferably uses, as the plasma, argon, xenon, neon, helium, krypton, nitrogen, oxygen, ammonium, hydrogen, or water vapor.

In the first material surface treating method, the base material is preferably a base material for a medical material. The polymer is preferably a biocompatible component. With such features, a base material which exhibits stable biocompatibility for a long term can be obtained, and a medical material with excellent biocompatibility can be realized.

The second material surface treating method of the present invention includes: a diamond-like carbon film formation step of forming a diamond-like carbon film on a surface of a base material; a plasma irradiation step of irradiating a surface of the diamond-like carbon film with plasma to generate a reactive region on the surface of the diamond-like carbon film; and a surface modification step of causing a reaction of the reactive region and a molecule containing oxygen to introduce a hydroxy group to the surface of the diamond-like carbon film.

The second material surface treating method includes the plasma irradiation step of irradiating a surface of the diamond-like carbon film with plasma to generate a reactive region on the surface of the diamond-like carbon film, and the surface modification step of causing a reaction of the reactive region and a molecule containing oxygen to introduce a hydroxy group to the surface of the diamond-like carbon film. Therefore, it is possible to change the surface of the DLC film to be hydrophilic. It is possible to realize a material with excellent biocompatibility. Since the hydroxy group can be further substituted, it is possible to freely introduce a functional group to the surface of the DLC film and modify the surface with various compounds.

Effects of the Invention

According to the present invention, a material wherein the surface of a base material is coated with a DLC film, and the DLC film is modified with a functionality component, typically a biocompatible material, stably for a long term, and a medical material and medical instrument with excellent biocompatibility can be realized.

BRIEF DESCRIPTION OF DRAWINGS

FIG. 3(a) shows the measurement result obtained before HMPA graft. FIG. 3(b) shows the measurement result obtained after HMPA graft.

Figure 1:
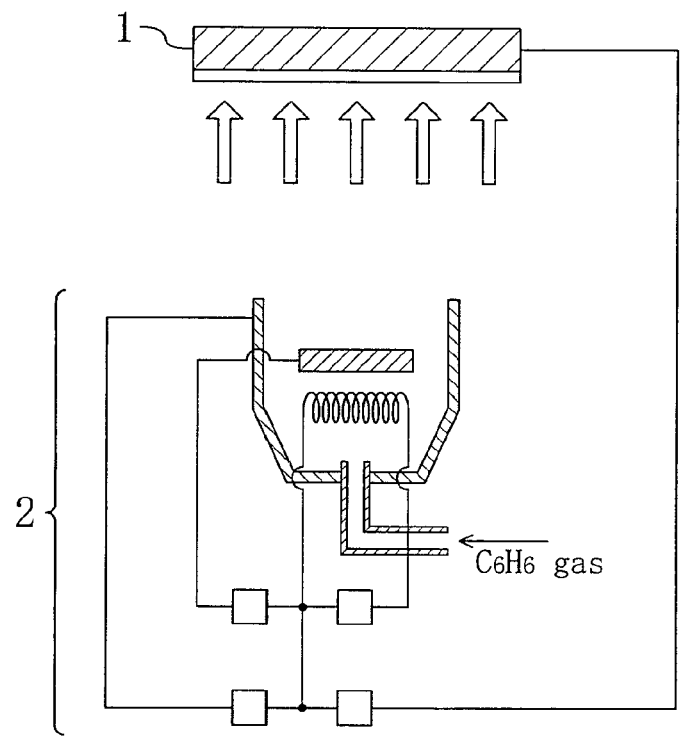
FIG. 1 is a schematic view of an ionic vapor deposition apparatus according to an embodiment of the present invention.

| Description of Reference Numerals | |
|---|---|
| 1 | Substrate |
| 2 | Arc Discharge Plasma Generator |
| 11 | Base Material |
| 21 | Chamber |
| 22 | Vacuum Pump |
| 23 | Electrode |
| 24 | Electrode |
| 25 | High Frequency Power Supply |
| 26 | Matching Network |

BEST MODE FOR CARRYING OUT THE INVENTION

The present inventors found that irradiating an inert DLC film, which has no reactivity in nature, with plasma, or the like, can activate the DLC film, so that monomers can be grafted to the surface of the DLC film by graft polymerization, or various functional groups can be introduced to the surface of the DLC film.

Thus, for example, after the surface of a DLC film formed on the surface of a base material, such as a metal, ceramic, resin, rubber, or the like, is activated, various functionality components are chemically bonded to the surface of the DLC film by means of graft polymerization, covalent bond, ionic bond, or the like, whereby the surface of the material is protected while various characteristics can be given to the material stably for a long term.

The present inventors also found that, when a biocompatible component is chemically bonded to the surface of the DLC film, a medical material which exhibits excellent biocompatibility for a long term can be realized wherein none of separation of the biocompatible component from the material surface and deterioration of the material occurs, and completed the present invention. Hereinafter, a structure of the present invention is described.

The base material used in the present invention is a metal material, a semiconductor material, such as silicon, or the like, a ceramic material, rubber, a polymeric material, such as a resin, or the like, or a complex thereof. The base material is subjected to various processes for medical uses, semiconductor uses, or other uses. For example, in medical uses, the base material of the present invention is used as a base material of a medical material used for manufacturing a medical instrument which comes in contact with a living body or organic component, typically a catheter, guide wire, stent, artificial cardiovalvular membrane, and artificial joint. The medical material includes materials used for medical instruments, such as wires, tubes, plates, etc., one that obtained by processing any of these materials in the shape of a medical instrument, and one that is in the midst of the formation of the medical instrument. As for semiconductor uses, the base material may be, for example, a semiconductor substrate which is a constituent of a semiconductor device.

Although the type of the base material is not limited to anything particular, a metal, such as iron, nickel, chrome, copper, titanium, platinum, tungsten, tantalum, or the like, can be used. Also, alloys of these metals, for example, stainless steel, such as SUS316L, or the like, a shape memory alloy, such as a Ti—Ni alloy, a Cu—Al—Mn alloy, or the like, other alloys, such as a Cu—Zn alloy, a Ni—Al alloy, a titanium alloy, a tantalum alloy, a platinum alloy, a tungsten alloy, or the like, can be used.

Alternatively, the base material may be a silicon or gallium semiconductor material, aluminum, silicon or zirconium oxide, silicon or zirconium nitride, ceramic or apatite, such as a carbide, or bioactive ceramic, such as bioglass, or the like. The base material may be a macromolecular resin, such as polymethyl methacrylate (PMMA), high density polyethylene, polyacetal, or the like, a silicon polymer, such as polydimethylsiloxane, or the like, or a fluoric polymer, such as polytetrafluoroethylene, or the like.

The DLC film formed on the surface of the base material is a film formed of diamond-like carbon (which may contain a very small amount of any other component as an impurity). This film is very smooth and inert in nature. However, free radicals or ion species can be generated by irradiating the surface of the DLC film with plasma, or the like, and cleaving some of diamond (carbon to carbon) bonds on the surface. Accordingly, a functionality component can be grafted by graft polymerization to the surface of the DLC film, or various functional groups can be introduced to the surface of the DLC film by means of reactions with various substances after activation.

Although the surface of the base material has irregularities on the order of microscale or nanoscale, formation of a DLC film on the surface of the base material can achieve a smooth surface. With the smooth surface, it is possible to uniformly irradiate the surface of the base material with plasma, so that uniform graft polymerization can be performed over the surface of the base material. Since the DLC film is a very dense and hard film, a foreign component can be prevented from permeating the DLC film and deteriorating the base material. Therefore, the material of the present invention can be used for a product used in an environment in which the acid resistance or alkali resistance is required or a product used in a living body.

In the present invention, the DLC film can be formed on the surface of the base material using a known method, such as sputtering, DC magnetron sputtering, RF magnetron sputtering, chemical vapor deposition (CVD), plasma CVD, plasma-based ion implantation, plasma-based ion implantation with superimposed RF and high-voltage pulses, ionic plating, arc ionic plating, ion beam deposition, laser ablation, or the like. The thickness of the DLC film is not limited to any particular thickness but is preferably in the range of 0.01 to 3 μm and, more preferably, in the range of 0.02 to 1 μm.

Although the DLC film can be directly formed on the surface of the base material, an intermediate layer may be provided between the base material and the DLC film for more firmly adhering the base material and the DLC film. The material of the intermediate layer can be selected among various materials according to the type of the base material. Any known material, such as an amorphous film of silicon (Si) and carbon (C), an amorphous film of titanium (Ti) and carbon (C), an amorphous film of chromium (Cr) and carbon (C), or the like, can be used for the intermediate layer. The thickness of the intermediate layer is not limited to any particular thickness but is preferably in the range of 0.005 to 0.3 μm and, more preferably, in the range of 0.01 to 0.1 μm.

The intermediate layer can be formed using a known method. For example, sputtering, CVD, plasma CVD, flame spraying, ionic plating, arc ionic plating, or the like, may be used.

According to the present invention, the surface of a DLC film is activated by energy irradiation on the DLC film with plasma, light, or the like, whereby a radical, ion, or the like, which serves as a polymerization starting point, can be generated on the surface of the DLC film. In the case of plasma irradiation, a gas capable of disconnecting a carbon to carbon bond present on the surface of the DLC film, such as argon (Ar), neon (Ne), helium (He), krypton (Kr), xenon (Xe), nitrogen gas (N₂), oxygen gas (O₂), ammonium gas (NH₄), hydrogen gas (H₂), water vapor (H₂O), or the like, or a mixture gas thereof can be used as a plasma gas source. Alternatively, the surface of the DLC film can be activated by means of irradiation with ultraviolet light or ultraviolet ozone.

The activated surface of the DLC film has radicals, or the like, which serve as polymerization starting points. Therefore, various organic components can be grafted to the surface of the DLC film by graft-polymerizing various radical-polymerizable monomers on the activated surface of the DLC film. Therefore, an addition-polymerizable monomer, such as a vinylmonomer having the general formula of Formula 1, a vinylidene monomer having the general formula of Formula 2, a vinylene monomer having the general formula of Formula 3, a cyclic vinylene monomer having the general formula of Formula 4, or the like, can be graft-polymerized at a polymerization starting point generated on the surface of the DLC film.

Since the polymerization starting points can be generated on only part of the surface of the DLC film subjected to energy irradiation, a polymer can be introduced by graft polymerization only at a desired position over the surface of the base material using an appropriate mask. Further, the density of the polymer on the surface of the base material can be freely adjusted. For example, in the case where antithrombogenicity is given to the base material, the adjustment of the surface density of an antithrombotic macromolecular material grafted to the surface of the DLC film is important. According to the present invention, the surface density is readily adjustable.

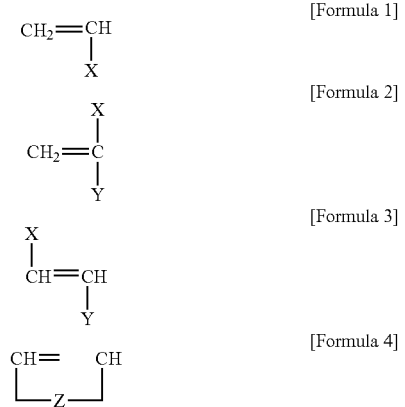

In the monomer structures of Formula 1 to Formula 3, substituents X and Y are ester or amido, typically —COOR₁, —CONR₂, or the like. Substituents X and Y in the same molecule may be identical or may be different. In the monomer structure of Formula 4, substituent Z is ester or amido which is a constituent of a cyclic structure and typically is —CO—O—CO—, —CO—NR₃—CO—, or the like.

Especially in the case where the material is applied to medical uses, R1 to R3 are each has a structure containing a highly biocompatible constituent, for example, a functional group, such as an ethyleneoxide group, hydroxy group, amino group, phosphorylcholine group, phosphate group, sulfone group, nucleobase, or the like, a monosaccharide, or a polysaccharide. It is preferably a molecule which forms a hydrogel layer at the interface with water when graft-polymerized.

Other than hydrophilic monomers, it may be a monomer containing dimethylsiloxane, fluorine, or the like, which is unlikely to adsorb protein and exhibits high hydrophobicity and biocomparibility.

Specifically, a known polymerizable monomer from which a biocompatible polymer is obtained when graft polymerized, such as 2-methacryloyl-oxyethyl phosphorylcholine (MPC), 2-acryloyl-oxyethyl phosphorylcholine, 1-methyl-2-methacryloyl-amideethyl phosphorylcholine, 2-glucoxy-oxyethyl methacryl acid, sulfated 2-glucoxy-oxyethyl methacryl acid, p-N-vinylbenzyl-D-lactone amide, p-N-vinylbenzyl-D-propione amide, p-N-vinylbenzyl-D-malto-trione amide, o-methacryloyl-L-serine, o-methacryloyl-L-threonine, o-methacryloyl-L-tyrosine, o-methacryloyl-L-hydroxyproline, 2-methoxyethyl methacryl amide, 2-methoxyethyl acryl amide, 2-hydroxyethyl acryl acid, 2-hydroxyethyl methacrylic acid, N-2-hydroxypropyl methacryl amide, N-isopropyl acryl amide, N-vinylpyrrolidone, vinylphenol, N-2-hydroxy acryl amide, acryl amide derivative monomer, methacryl amide derivative monomer, phospholipid-like vinylmonomer, macromonomer of polyethylenoxyde, or the like, can be used.

For example, a hydrogel layer, which has the function of inhibiting recognition of a foreign substance by a living body similarly to the surface of a biomembrane, can be formed on the surface of a DLC film by introducing MPC to the surface of the DLC film by graft polymerization. Since phospholipid present in blood is oriented/disposed on the basis of MPC grafted to the surface of the DLC film as a core, a function similar to that of the biomembrane can be given to the surface of the DLC film.

The above-listed monomers may be solely graft-polymerized or may be graft-polymerized in the form of a multidimensional copolymer. The graft polymerization may be performed at a single step or may be repeatedly performed in multi steps.

Although the optimum molecular weight of a polymer obtained by the graft polymerization depends on the use of the material, the type of a monomer to be grafted, etc., the component to be grafted to the surface is not limited to a macromolecule but may be an oligomer where the molecular weight of the polymer is 1000 or less. Especially when the material is applied to a medical use, the component may be one that the characteristics, such as the surface wettability of the material, etc., are changeable.

Although the above-described example uses radical polymerization, the graft can be achieved with anion polymerization or cation polymerization instead of radical polymerization by generating cation species or anion species as polymerization starting points on the surface of the DLC film. These polymerization starting points can be generated by means of low-temperature plasma irradiation, ultraviolet or ultraviolet ozone irradiation, γ-ray, or the like.

The method for modifying with a functionality component the surface of the DLC film which serves as a coating over the surface of the base material is not limited to the graft polymerization of monomers. For example, the technique of grafting a molecular chain may be employed wherein, for example, a functional group, such as an amino group, a carboxyl group, or the like, is introduced to the surface of the DLC film, and the functional group introduced to the surface of the DLC film and a functional group of the molecular chain are brought into a reaction.

The surface of the DLC film is activated by, for example, a plasma treatment so that an active point, such as a radical, or the like, is generated, and then, the active point is brought into a reaction with water or oxygen, whereby a hydroxy group can readily be introduced to the surface of the DLC film.

The hydroxy group introduced to the surface of the DLC film can readily be converted into an amino group, a carboxyl group, an isocyanate group, or a vinyl group by means of a reaction with a functional alkoxy silane derivative, such as 3-aminopropyltrimethoxysilane, or the like, a functional carboxylic acid, such as 2-mercaptoacetic acid, or the like, a diisocyanate derivative, 2-methacryloyl-oxyethyl isocyanate, 2-acryloyl-oxyethyl isocyanate, N-methacryloyl-succinimide, or N-acryloyl-succinimide. A functionality component containing in the molecule a functional group which cause a reaction with the functional group introduced to the surface of the DLC film, for example, an amino group, a carboxyl group, an isocyanate group, or a trialkyloxysilane group such as trimethoxysilane, triethoxysilane, etc., can readily be covalent-bonded to the surface of the DLC film. Even when the functionality component does not include a functional group which causes a direct reaction with the functional group on the surface of the DLC film, a functional group can be covalent-bonded to the surface of the DLC film by using a bifunctional reagent.

Especially when the material is applied to a medical use, a tissue-derived component having a functional group, such as peptide, protein, nucleobase, sugar chain, chitin, chitosan, or the like, or a biocompatible macromolecular chain including a hydroxy group, a carboxyl group, or amino group introduced by chain transfer reaction at a terminal may be brought into a coupling reaction with a functional group introduced to the surface of the DLC film in advance and fixed by covalent bond. The functionality component is not limited to a macromolecular chain but may be a low molecular component, such as an amino acid and a monosaccharide, and oligomers thereof. The reaction for converting the functional group is not limited to a single step reaction but may be a multi-step reaction. For example, the functional group may be converted in multi steps such that a hydroxy group is converted to an amino group and then to a vinyl group.

A biocompatible component may be introduced to the surface of the DLC film by forming an ionic bond between the surface of the DLC film and the biocompatible component using an ionic functional group present in the biocompatible component, such as a carboxyl group, amino group, phosphate group, or the like. In this case, the biocompatible component can readily be introduced to the surface of the DLC film even if it is an inorganic component, such as hydroxyapatite, or the like.

Biocompatibility may be given to the DLC film itself by introducing a functional group to the surface of the DLC film to alter the surface of the DLC film into a hydrophilic surface instead of introducing another biocompatible component to the surface of the DLC film.

EXAMPLE

Hereinafter, the present invention is described in more detail along with an example but is not limited to this example in any respect.

---Coating with DLC Film---

Coating of a DLC film over the base material is first described. In this example, an aluminum alloy (equivalent to JIS-8021 alloy) having a length of 50 mm, a width of 5 mm, and a thickness of 55 μm and polyethylene terephthalate (PET) were used for the base material.

FIG. 1 is a schematic view of an ionic vapor deposition apparatus used in this example. The ionic vapor deposition apparatus is a commonly-employed ionic vapor deposition apparatus wherein benzene ($C_6H_6$) gas is introduced as a carbon source into a DC arc discharge plasma generator 2 provided inside a vacuum chamber to generate plasma, and the generated plasma is collided with a substrate 1 biased to a negative voltage, which is a subject of the coating, whereby the plasma is solidified over the substrate 1 to form a film.

The base material was set inside the chamber of the ionic vapor deposition apparatus shown in FIG. 1, and argon gas (Ar) at the pressure of $10^{-3}$ to $10^{-5}$ Torr was introduced into the chamber, and then, a bombardment cleaning was carried out for about 30 minutes wherein Ar ions were generated by electric discharge, and the generated Ar ions were collided with the surface of the base material.

Then, tetramethylsilane ($Si(CH_3)_4$) was introduced into the chamber to form, as an intermediate layer, an amorphous film having a thickness of 0.02 μm to 0.05 μm containing silicon (Si) and carbon (C) as primary constituents.

After the formation of the intermediate layer, $C_6H_6$ gas was introduced into the chamber, and the gas pressure was set to $10^{-3}$ Torr. Electric discharge was performed while $C_6H_6$ was continuously introduced at the rate of 30 ml/min to ionize $C_6H_6$. Then, ionic vapor deposition was performed for about 10 minutes to form a DLC film having a thickness of 0.1 μm over the surface of the base material.

The formation of the DLC film was carried out under the following conditions: Substrate Voltage 1.5 kV, Substrate Current 50 mA, Filament Voltage 14 V, Filament Current 30 A, Anode Voltage 50V, Anode Current 0.6 A, Reflector Voltage 50 V, Reflector Current 6 mA. The temperature of the substrate was about 160° C.

The intermediate layer was provided for improving the adherence between the base material and the DLC film but may be omitted if sufficient adherence can be secured between the base material and the DLC film.

In this example, $C_6H_6$ gas was solely used as the carbon source, but mixture gas of $C_6H_6$ and fluorocarbon gas, such as $CF_4$, or the like, may be used for forming a DLC film containing fluorine over the surface of the base material.

---Activation of DLC Film---

Figure 2:
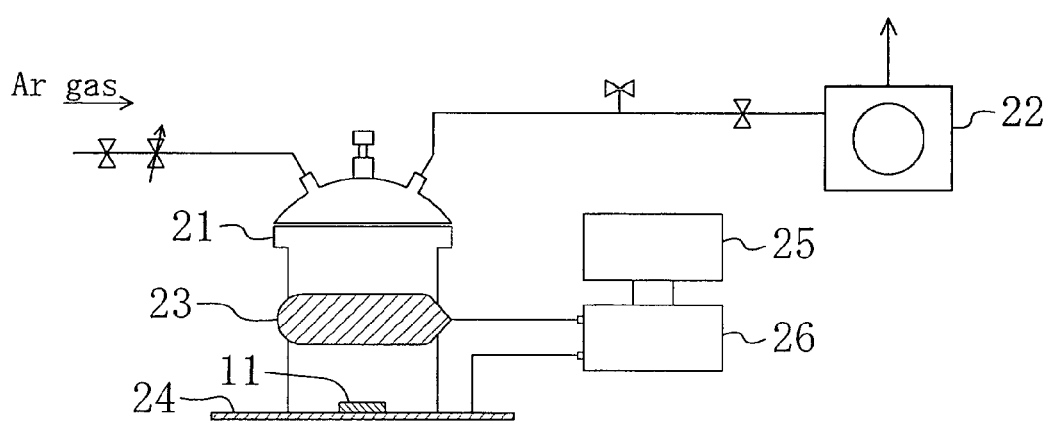
FIG. 2 is a schematic view of a plasma irradiation apparatus which is used for a medical material production method according to an embodiment of the present invention.

The DLC film formed over the surface of the base material was irradiated with plasma to activate the surface, and then a functionality component was grafted to the surface of the DLC film. FIG. 2 is a schematic view of a plasma irradiation apparatus used in this example.

As shown in FIG. 2, the plasma irradiation apparatus is a commonly-employed plasma irradiation apparatus wherein a chamber 21 formed by a separable flask, to which a vacuum pump 22 is connected and with which gas replacement is possible, is provided with electrodes 23 and 24 at the barrel and bottom, respectively, and a high frequency wave is applied to the electrodes through a matching network from a high frequency source 26 to generate plasma inside the chamber 21.

Firstly, the base material 11 with the DLC film formed thereon was set inside the chamber 21 of the plasma irradiation apparatus, and Ar gas was introduced so that the inner pressure of the chamber 21 was 1.3 Pa. Then, a high frequency wave of 20 W was applied to the electrodes 23 and 24 using the high frequency source 26 (JRF-300 manufactured by JEOL Ltd.; Frequency 13.56 MHz) to generate plasma inside the chamber 21. The DLC film formed on the base material 11 was irradiated with the plasma for about 2 minutes to produce radicals on the surface of the DLC film.

---Graft to DLC Film---

In this example illustrated herein, hydrophilic 2-hydroxypropyl methacryl amide (HPMA) was grafted to the activated DLC film.

After the plasma irradiation, the base material was exposed to air for about 1 minute and then inserted into a glass polymerization tube together with 10 ml of ethanol solution of HPMA (concentration: 0.17 g/ml). The cycle of freezing-deaeration-nitride replacement in liquid nitrogen was repeated several times to purge dissolved oxygen from the polymerization tube. Thereafter, the polymerization tube was sealed under a reduced pressure, and polymerization was carried out at 80° C. for 24 hours, whereby HPMA was graft-polymerized over the surface of the DLC film to graft the polymer of HPMA.

After the polymerization, the base material was immersed into an abundant amount of ethanol and then washed with an abundant amount of phosphoric acid buffer solution (pH=7.4) before freeze drying. As a result, a graft base material with a grafted HPMA polymer was obtained. It should be noted that, after the plasma irradiation, the base material is not necessarily exposed to air.

We measured the composition of elements present at the surface of the obtained graft base material using X-ray photoelectron spectroscopy (XPS) and confirmed introduction of HPMA. The XPS measurement was carried out using a XPS/ESCA apparatus, Model 5600 CiMC, manufactured by Perkin Elmer, Inc., and the X-ray source was a monochromatized Alk$\alpha$ (1486.5 eV) at the power of 100 w (14 kV, 7 mA). In the measurement, a neutralizer was used as a neutralizing electron gun, and the depth of the measurement was 4 nm.

Figure 3A:
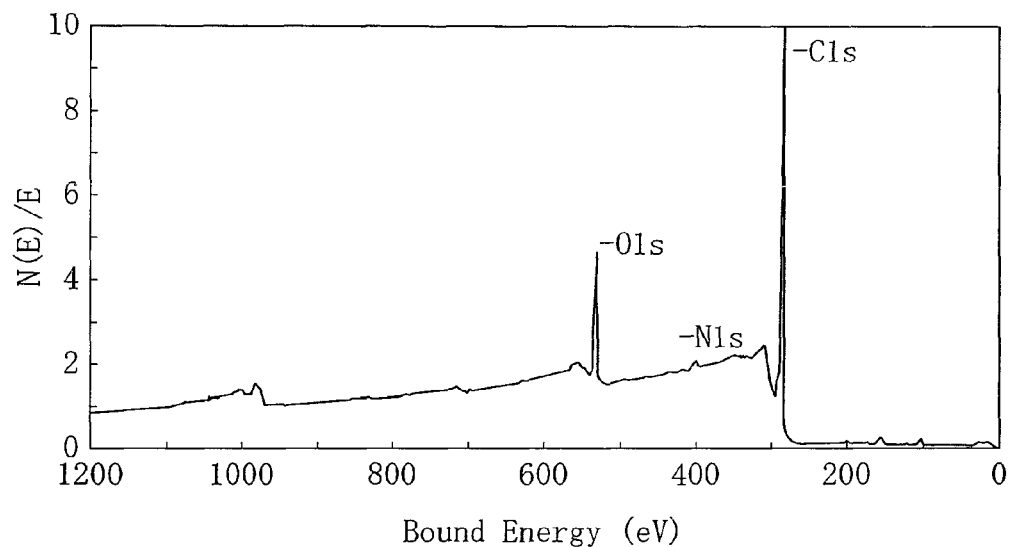
FIG. 3(a) and FIG. 3(b) show results of XPS measurement of the surface of a DLC film formed on a base material of aluminum based on a medical material production method according to an embodiment of the present invention.
Figure 3B:
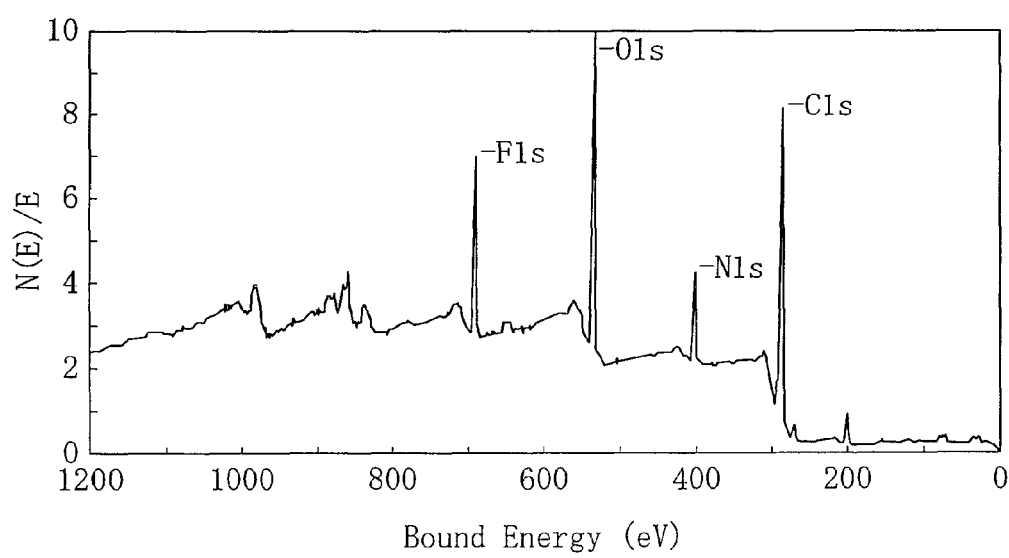

FIG. 3 shows the results of XPS measurement of the distribution of elements present at the surface of a DLC film formed on a base material of aluminum. FIG. 3(a) shows the result of a base material surface measurement before a HPMA polymer was grafted. FIG. 3(b) shows the result of a base material surface measurement after the HPMA polymer was grafted.

Referring to FIG. 3(b), as for the DLC film surface after the HPMA polymer graft, we found the 1 s peak of nitrogen (N), which was not seen before the graft (FIG. 3(a)). The constitution ratio of carbon (C), oxygen (O), and nitrogen (N) obtained from the peak areas was C, 85.1%; O, 13.93%; N, 0.89% before the graft, but C, 85.1%; O, 13.93%; N, 0.89% after the graft. That is, nitrogen (N) and oxygen (O) were greatly increased with respect to carbon (C). This indicates that a HPMA polymer was grafted to the surface of the DLC film and, as a result, an amido group was introduced to the surface of the DLC film.

We also grafted a HPMA polymer to a DLC film formed on a base material of PET and carried out the above-described measurement on this sample. We also found the 1s peak of nitrogen after the HPMA polymer graft, which was not seen before the graft, and confirmed introduction of the HPMA polymer as in the case of the aluminum base material.

Then, the wettability of the surface of the obtained graft base material was measured using a contact angle measurement apparatus. The measurement of the contact angle was carried out using a goniometer-based contact angle measurement apparatus G-I manufactured by ERMA Inc.), wherein a water drop of 15 μl was placed on the surface of the medical material, and 50 seconds later, the left contact angle was measured, and 70 seconds later, the right contact angle was measured. The measurement value was the average of values at 10 measurement points.

In the case where a HPMA polymer was grafted to the surface of the DLC film formed on the aluminum base material, the contact angle of 67.8±3.5° before the graft of the HPMA polymer was decreased to 51.8±3.0° after the graft. This indicates that the HPMA polymer grafted to the surface of the DLC film changed the surface to be hydrophilic, thereby improving the biocompatibility of the graft base material.

In the case of the PET base material, the contact angle of 80.2±2.2° before the graft of the HPMA polymer was decreased to 52.1±2.5° after the graft. This indicates that the surface was changed to be hydrophilic as was in the case of the aluminum base material.

As described above, a polymer of HPMA is grafted to the surface of a DLC film formed on a medical material so that the surface of the DLC film becomes hydrophilic, whereby a hydrogel layer which inhibits foreign substance recognition by a living body is formed on the surface of the DLC film. Therefore, the biocompatibility of the medical material is improved. Since the HPMA polymer is introduced to the surface of the DLC film by graft polymerization so as not to readily separate, stable biocompatibility can be maintained for a long term.

By using the procedure of this example, a hydrophilic hydroxy group can be introduced to the surface of a DLC film. A DLC film was treated with plasma according to the procedure of this example and subjected to an exposure treatment in air for 2 minutes. The resultant sample was subjected to the XPS measurement and contact angle measurement. In the XPS measurement, we saw a C1s peak based on C—O bonds near 287 eV, which was not seen in an untreated DLC film, and confirmed introduction of a hydroxy group. The contact angle of 79.2±3.0° before the plasma treatment was decreased to 69.8±3.2° after the plasma treatment, which means an improvement in the wettability of the surface of the DLC film. This indicates that exposure of the plasma-treated DLC film to air caused a reaction of radicals produced at the surface of the DLC film and oxygen in air, whereby a hydroxy group was introduced to the surface of the DLC film.

As described above, according to the present invention, it is possible to cover the surface of a base material with an inert DLC film and freely modify the surface of the DLC film with various molecules. With this, it is possible not only to improve the durability of the base material but also to give a functionality of a molecule with which the surface of the DLC film is modified. For example, if the DLC film is modified with a molecule having the function of biocompatibility, a medical material which exhibits high durability and stable biocompatibility for a long term is obtained. Alternatively, by grafting stimuli-sensitive biocompatible gel to the surface of a DLC film, it is possible to achieve a cell culture material which causes less damage when separated or a highly-active bioreactor material.

Still alternatively, for example, the surface of a semiconductor substrate, such as a silicon, or the like, is coated with a DLC film, and then, a polymer is graft-polymerized to the DLC film, whereby the polymer is stably introduced to the surface of the semiconductor substrate. The resultant material can be used for an organic semiconductor device wherein molecular recognition is performed at the surface of the substrate. Since it is possible not only to perform the graft over the entire surface of the DLC film but also to perform the graft in an arbitrary pattern, the material can be applied to a microsensor which is used for measurement of a minute amount of substance, or the like.

Industrial Applicability

According to a material surface treatment method, surface-treated material, medical material, and medical instrument of the present invention, a material with a coating of diamond-like carbon film can be realized wherein the surface of a base material is coated with a diamond-like carbon film, and the diamond-like carbon film is modified with a functionality component, such as a biocompatible component, or the like, stably for a long term. Therefore, the present invention is useful not only as a method for treating the surface of a material with a diamond-like carbon film formed thereon and a surface-treated material but also as a medical material with excellent biocompatibility and a medical instrument formed of the medical material. Further, it is possible to give the material a functionality other than biocompatibility. The present invention is also useful as a material for an organic semiconductor device, or the like.

The invention claimed is:

1. A method for fabricating a material, the method comprising:
   a diamond-like carbon film formation step of forming a diamond-like carbon film on a surface of a base material;
   an activation step of generating on a surface of the diamond-like carbon film a reactive region which serves as a polymerization starting point; and
   a polymerization step of polymerizing monomers using the polymerization starting point to graft the monomers to the surface of the diamond-like carbon film, wherein said monomers are polymerized by the polymerization starting point generated by cleaving a carbon to carbon bond present on the surface of the diamond-like carbon film.

2. The method of claim 1, wherein
the polymerization starting point is a free radical generated by cleaving a carbon to carbon bond present on the surface of the diamond-like carbon film.

3. The method of claim 1, wherein
the activation step is a plasma irradiation step of irradiating the surface of the diamond-like carbon film with plasma.

4. The method of claim 3, wherein
the plasma irradiation step uses, as the plasma, argon, xenon, neon, helium, krypton, nitrogen, oxygen, hydrogen, or water vapor.

5. The method of claim 1, further comprising,
a mask formation step of forming a mask for selectively exposing a surface of the diamond-like carbon film after the diamond-like carbon film formation step and before the activation step, wherein
the polymerization starting point is formed in an exposed part of the diamond-like carbon film.

6. The method of claim 1, wherein
the monomer is a vinylmonomer, vinylidene monomer, vinylene monomer, or cyclic vinylene monomer.

7. The method of claim 1, wherein
the monomer includes fluorine and silicone.

8. The method of claim 1, wherein
the base material is a medical material, and
the polymer is a biocompatibility component.

9. The method of claim 1, wherein
the base material is a material of a catheter, guide wire, stent, artificial cardiovalvular membrane, or artificial joint.

10. The method of claim 1, wherein
the polymer contains at least one functional group selected from the group consisting of an ethylene oxide group, a hydroxy group, a phosphate group, an amino group, an amido group, a phosphorylcholine group, a sulfone group, and a carboxyl group.

11. The method of claim 1 wherein,
the monomer is a 2-methacryloyl-oxyethyl phosphorylcholine, 2-acryloyl-oxyethyl phosphorylcholine, 1-methyl-2-methacryloyl-amideethyl phosphorylcholine, 2-glucoxy-oxyethyl methacryl acid, sulfated 2-glucoxy-oxyethyl methacryl acid, p-N-vinylbenzyl-D-lactone amide, p-N-vinylbenzyl-D-propione amide, p-N-vinylbenzyl-D-malto-trione amide, o-methacryloyl-L-serine, o-methacryloly-L-threonine, o-methacryloyl-L-tyrosine, o-methacryloyl-L-hydroxyproline, 2-methoxyethyl methacryl amide, 2-methoxyethyl acryl amide, 2-hydroxyethyl acryl acid, 2-hydroxyethyl methacrylic acid, N-2-hydroxypropyl methacryl amide, N-isopropyl acryl aminde, N-vinylpyrrolidone, vinylphenol, or N-2-hydroxy acryl amide.

12. The method of claim 1, further comprising
an intermediate layer formation step of forming an intermediate layer for improving adherence between the base material and the diamond-like carbon film on the surface of the base material before the diamond-like carbon film formation step, wherein
in the intermediate layer formation step, the intermediate layer is formed of an amorphous film containing titanium and carbon or chromium and carbon as primary constituents.

13. A method of fabricating a material, the method comprising:
   a diamond-like carbon film formation step of forming a diamond-like carbon film on the surface of a base material;
   a plasma irradiation step of irradiating a surface of the diamond-like carbon film with plasma to generate a reactive region on the surface of the diamond-like carbon film; and
   a surface modification step of causing a reaction of the reactive region and a molecule containing oxygen to introduce a hydroxy group to the surface of the diamond-like carbon film, wherein
   in the surface modification step, the molecule containing oxygen is reacted with a radical formed by cleaving a carbon to carbon bond present on the surface of the diamond-like carbon film.

14. The method step of claim 13, further comprising
a fixture step of fixing a biocompatible component on the surface of the diamond-like carbon film through the hydroxy group.

15. The method of claim 1, wherein
in the polymerization step, the diamond-like carbon film activated is reacted with a solution which contains monomers and does not contain an initiator.

* * * * *

UNITED STATES PATENT AND TRADEMARK OFFICE
CERTIFICATE OF CORRECTION

PATENT NO. : 8,221,823 B2 Page 1 of 1
APPLICATION NO. : 12/697581
DATED : July 17, 2012
INVENTOR(S) : Yoshinori Abe et al.

It is certified that error appears in the above-identified patent and that said Letters Patent is hereby corrected as shown below:

ON THE TITLE PAGE:

At item (56), References Cited, under OTHER PUBLICATIONS (in the right-hand column), after "Gutensohn, K., et al., ... Thrombosis Research 99 (2000) 577-585.*", insert the following:

--NAKATANI, Tatsuyuki, et al., "Imparting Superhydrophilicity to Diamond-Like Carbon by Plasma Surface Treatment Technique", New Diamond and Frontier Carbon Technology, Vol. 17, No. 6, 2007, pp. 289-300.*--

Signed and Sealed this
Sixth Day of November, 2012

David J. Kappos
*Director of the United States Patent and Trademark Office*